US012239783B2

United States Patent
Downs, III et al.

(10) Patent No.: US 12,239,783 B2
(45) Date of Patent: Mar. 4, 2025

(54) BREATHING GAS REMIXER

(71) Applicant: Emercent Technologies LLC, Rochester, MN (US)

(72) Inventors: J. Hunter Downs, III, Rochester, MN (US); Bruce D. Johnson, Rochester, MN (US)

(73) Assignee: Emercent Technologies LLC, Rochester, MN (US)

( * ) Notice: Subject to any disclaimer, the term of this patent is extended or adjusted under 35 U.S.C. 154(b) by 817 days.

(21) Appl. No.: 17/223,582

(22) Filed: Apr. 6, 2021

(65) Prior Publication Data

US 2021/0308396 A1 Oct. 7, 2021

Related U.S. Application Data

(60) Provisional application No. 63/005,658, filed on Apr. 6, 2020.

(51) Int. Cl.
| | |
|---|---|
| *A61M 16/00* | (2006.01) |
| *A61M 16/06* | (2006.01) |
| *A61M 16/12* | (2006.01) |
| *A61M 16/20* | (2006.01) |

(52) U.S. Cl.
CPC .... *A61M 16/0045* (2013.01); *A61M 16/0003* (2014.02); *A61M 16/06* (2013.01); *A61M 16/125* (2014.02); *A61M 16/208* (2013.01); *A61M 2202/0225* (2013.01); *A61M 2205/52* (2013.01); *A61M 2205/8206* (2013.01)

(58) Field of Classification Search
CPC .......... A61M 16/0045; A61M 16/0003; A61M 16/125; A61M 16/06; A61M 16/208; A61M 16/03; A61M 16/0125; A61M 16/0208; A61M 2016/103
See application file for complete search history.

(56) References Cited

U.S. PATENT DOCUMENTS

| | | | |
|---|---|---|---|
| 4,231,359 A * | 11/1980 | Martin | A62B 17/04 128/206.29 |
| 6,269,810 B1 * | 8/2001 | Brooker | A61M 15/0065 128/203.29 |
| 10,226,591 B1 * | 3/2019 | Tarler | A61M 16/022 |
| 2005/0103338 A1 | 5/2005 | Bunke et al. | |
| 2005/0247311 A1 | 11/2005 | Vacchiano et al. | |
| 2006/0130839 A1 * | 6/2006 | Bassovitch | A61M 16/0045 128/914 |

(Continued)

OTHER PUBLICATIONS

H. Benallal et al., Evaluation of cardiac output from a tidallly ventilated homogeneous lung model, Eur J Appl Physiol (2005) 95: 153-162.

*Primary Examiner* — Margaret M Luarca
(74) *Attorney, Agent, or Firm* — Headland Law & Strategy; Matthew J. Smyth

(57) ABSTRACT

Aspects discussed herein relate to remixing devices that can be used to modify a gas mix being inhaled by a user. The device can accurately adjust inspired $CO_2$ and/or $O_2$ levels independently to a desired level. Aspects described herein generally improve the quality, efficiency, and speed of devices to provide breathing gas mixes. Medical conditions can be diagnosed and a therapeutically effective gas mix can be provided as treatment for diagnosed medical conditions.

10 Claims, 9 Drawing Sheets

(56) References Cited

U.S. PATENT DOCUMENTS

| | | | |
|---|---|---|---|
| 2007/0163587 A1* | 7/2007 | Teibel | A61M 16/1065 |
| | | | 128/205.27 |
| 2008/0121233 A1 | 5/2008 | von Blumenthal et al. | |
| 2012/0060841 A1* | 3/2012 | Crawford, Jr. | A61M 16/125 |
| | | | 128/205.11 |
| 2012/0215081 A1* | 8/2012 | Euliano | A61M 16/026 |
| | | | 600/323 |
| 2014/0171817 A1* | 6/2014 | Blanch | A61M 16/0051 |
| | | | 128/204.23 |
| 2015/0314145 A1* | 11/2015 | Squibb | A62B 9/02 |
| | | | 128/204.21 |
| 2015/0320951 A1 | 11/2015 | Acker et al. | |
| 2015/0352306 A1* | 12/2015 | Scheiner | A61M 16/0672 |
| | | | 128/205.25 |
| 2016/0213879 A1* | 7/2016 | Parthasarathy | A61M 16/208 |
| 2017/0000965 A1 | 1/2017 | Cortez, Jr. et al. | |
| 2018/0110946 A1* | 4/2018 | Palou Fustè | A61M 16/06 |
| 2019/0091425 A1* | 3/2019 | Figley | A61M 16/024 |

\* cited by examiner

BREATHING GAS REMIXER

CROSS-REFERENCE TO RELATED APPLICATIONS

The instant application claims priority to U.S. Provisional Patent Application No. 63/005,658, titled "Breathing Gas Remixer" and filed Apr. 6, 2020, the disclosure of which is hereby incorporated by reference in its entirety.

FIELD OF USE

Aspects of the disclosure relate generally to gas mixing and more specifically to devices for gas remixing.

BACKGROUND

Breathing systems can include open circuit, closed circuit, and semi-closed circuit systems. In open-circuit systems, all of the exhaled air is exhausted to the ambient environment. In closed-circuit systems, exhaled air is recaptured and recycled through a breathing loop. Closed-circuit systems typically supply a combination of gases to the breathing loop and include oxygen monitoring systems to monitor and adjust oxygen levels to guard against oxygen toxicity or hypoxia. In semi-closed circuit systems, a portion of the exhaled air is exhausted from the rebreather loop to the ambient environment and the remainder is recaptured and recycled through the breathing loop.

SUMMARY

The following presents a simplified summary of various aspects described herein. This summary is not an extensive overview, and is not intended to identify key or critical elements or to delineate the scope of the claims. The following summary merely presents some concepts in a simplified form as an introductory prelude to the more detailed description provided below. Corresponding apparatus, systems, and computer-readable media are also within the scope of the disclosure.

Aspects discussed herein relate to remixing devices that can be used to modify a gas mix being inhaled by a user. The device can accurately adjust inspired $CO_2$ and/or $O_2$ levels independently to a desired level. Aspects described herein generally improve the quality, efficiency, and speed of devices to provide breathing gas mixes. Medical conditions can be diagnosed and a therapeutically effective gas mix can be provided as treatment for diagnosed medical conditions.

These features, along with many others, are discussed in greater detail below.

BRIEF DESCRIPTION OF THE DRAWINGS

The present disclosure is illustrated by way of example and not limited in the accompanying figures in which like reference numerals indicate similar elements and in which.

DETAILED DESCRIPTION

Figure 1:
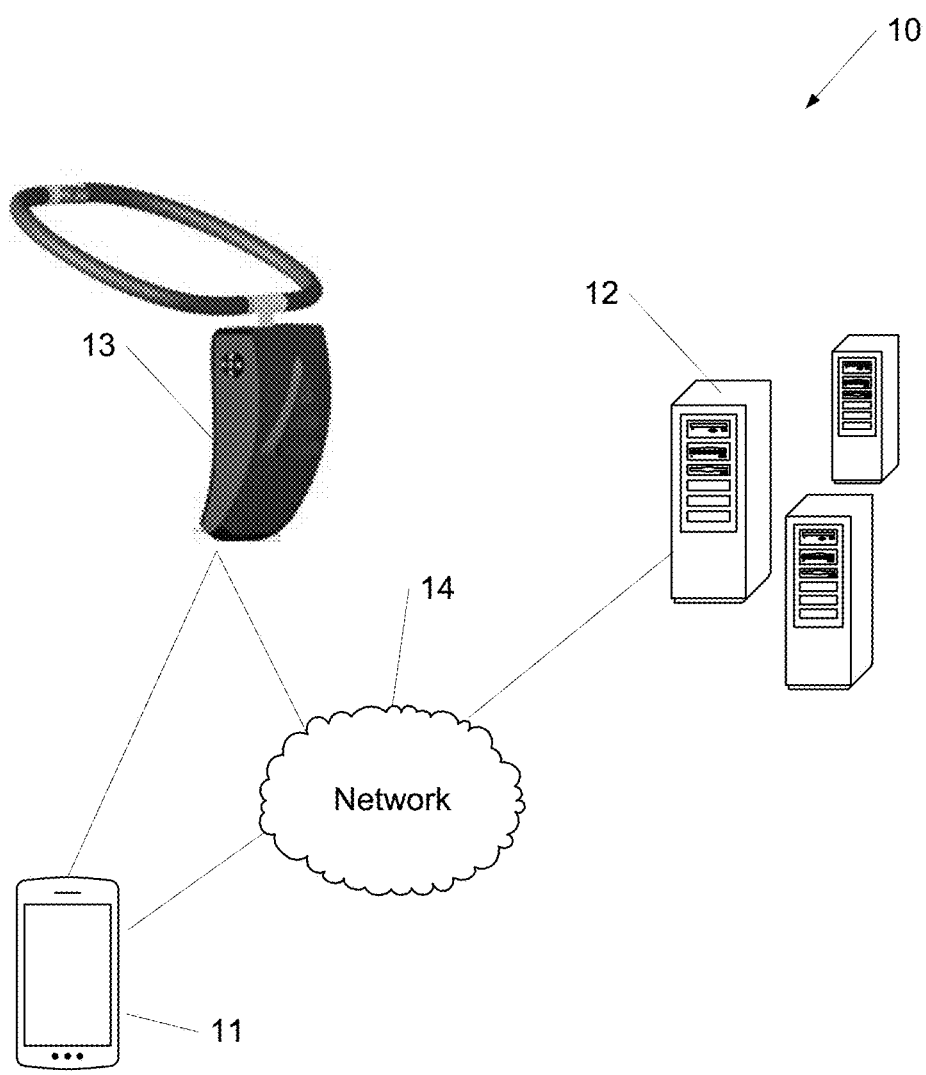
FIG. 1 illustrates an example of an operating environment in which one or more aspects described herein can be implemented.

In the following description of the various embodiments, reference is made to the accompanying drawings, which form a part hereof, and in which is shown by way of illustration various embodiments in which aspects of the disclosure can be practiced. It is to be understood that other embodiments can be utilized and structural and functional modifications can be made without departing from the scope of the present disclosure. Aspects of the disclosure are capable of other embodiments and of being practiced or being carried out in various ways. In addition, it is to be understood that the phraseology and terminology used herein are for the purpose of description and should not be regarded as limiting. Rather, the phrases and terms used herein are to be given their broadest interpretation and meaning.

By way of introduction, aspects discussed herein relate to providing breathing gas mixes and treating medical conditions. Blood flow can be increased and/or decreased by changing the concentration of certain gases, such as carbon dioxide ($CO_2$) within gas inhaled by an animal and/or human. Breathing gas remixers can capture the exhaled air, remix the captured air with fresh air in order to adjust the concentration of gases, particularly $CO_2$ relative to oxygen, and then provide the remixed gas for inhalation by the same animal. However, it should be noted that the concentration of any gas, such as nitrogen, can also be remixed in accordance with the requirements of specific embodiments of the invention.

Breathing gas remixers can be used to adjust the gas inhaled by animals, which can be used in the treatment of a variety of diagnosed conditions, such as vascular dementias. For example, Alzheimer's disease is commonly associated with beta amyloid plaque buildup in the brains of affected patients. Plaque buildup in a person's vascular system is commonly associated with decreased blood flow. For example, plaques in a person's brain may be associated with decreased cerebral blood flow. Similarly, deposits within other parts of a person's blood vessels may also be associated with decreased blood flow. Decreased blood flow can occur for a variety of reasons, such as old age and other conditions. Breathing gas remixers are designed to be used across a spectrum of needs, from athlete training to treating chronic diseases and recovery from conditions (e.g., stroke, MI, concussion, and the like). Increasing blood flow in patients with decreased blood flow can limit the buildup of plaque and/or clear existing plaque buildups or other senescent cells. Increasing blood flow can also stimulate vascular endothelial cells to improve the general blood flow. Based on a medical diagnostic for patients with compromised blood flow, one or more treatment plans can be identified. For example, a breathing gas remixer can be used to treat a patient with plaque deposits near the patient's blood vessels by administering a therapeutically effective dose of remixed gas to increase the patient's blood flow to volumes sufficient to limit and/or remove plaque deposits near the patient's blood vessels. In another example, breathing gas remixers can be used to increase blood flow for an athlete during training, increasing the effectiveness of the training regimen. In particular, treatments administered using a breathing gas remixer can stimulate central chemoreceptors, which is a form of motor neuronal training for the respiratory system.

Operating Environments and Computing Devices

FIG. 1 illustrates an operating environment 10 in accordance with an embodiment of the invention. The operating environment 10 includes at least one mobile device 11, a breathing gas remixer 13, and/or at least one processing server system 12 in communication via a network 14. It will be appreciated that the network connections shown are illustrative and any means of establishing a communications link between the computers can be used. The existence of any of various network protocols such as TCP/IP, Ethernet, FTP, HTTP and the like, and of various wireless communication technologies such as GSM, CDMA, WiFi, and LTE, is presumed, and the various computing devices described herein can be configured to communicate using any of these network protocols or technologies. Any of the devices and systems described herein can be implemented, in whole or in part, using one or more computing devices described with respect to FIG. 2.

Mobile devices 11 can provide data to and/or obtain data from the at least one processing server system 12 and/or breathing gas remixer 13 as described herein. Processing server systems 12 can store and process a variety of data as described herein. The breathing gas remixer 13 can measure breathing gas mixes, transmit and receive data, and/or provide breathing gas mixes as described herein. The network 14 can include a local area network (LAN), a wide area network (WAN), a wireless telecommunications network, and/or any other communication network or combinations thereof.

Some or all of the data described herein can be stored using any of a variety of data storage mechanisms, such as databases. These databases can include, but are not limited to relational databases, hierarchical databases, distributed databases, in-memory databases, flat file databases, XML databases, NoSQL databases, graph databases, and/or a combination thereof. The data transferred to and from various computing devices in the operating environment 100 can include secure and sensitive data, such as confidential documents, customer personally identifiable information, and account data. It can be desirable to protect transmissions of such data using secure network protocols and encryption and/or to protect the integrity of the data when stored on the various computing devices. For example, a file-based integration scheme or a service-based integration scheme can be utilized for transmitting data between the various computing devices. Data can be transmitted using various network communication protocols. Secure data transmission protocols and/or encryption can be used in file transfers to protect the integrity of the data, for example, File Transfer Protocol (FTP), Secure File Transfer Protocol (SFTP), and/or Pretty Good Privacy (PGP) encryption. In many embodiments, one or more web services can be implemented within the various computing devices. Web services can be accessed by authorized external devices and users to support input, extraction, and manipulation of data between the various computing devices in the operating environment 100. Web services built to support a personalized display system can be cross-domain and/or cross-platform, and can be built for enterprise use. Data can be transmitted using the Secure Sockets Layer (SSL) or Transport Layer Security (TLS) protocol to provide secure connections between the computing devices. Web services can be implemented using the WS-Security standard, providing for secure SOAP messages using XML encryption. Specialized hardware can be used to provide secure web services. For example, secure network appliances can include built-in features such as hardware-accelerated SSL and HTTPS, WS-Security, and/or firewalls. Such specialized hardware can be installed and configured in the operating environment 100 in front of one or more computing devices such that any external devices can communicate directly with the specialized hardware.

Figure 2:
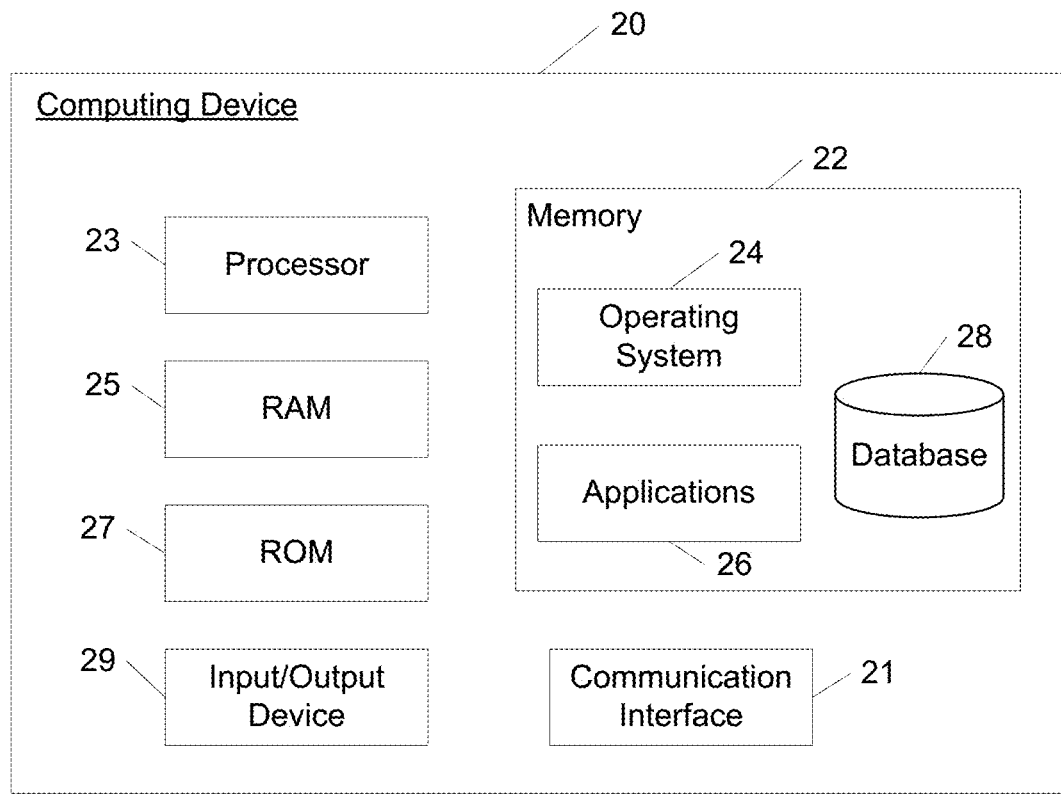
FIG. 2 illustrates an example computing device in accordance with one or more aspects described herein.

Turning now to FIG. 2, a computing device 20 in accordance with an embodiment of the invention is shown. The computing device 20 can include a processor 23 for controlling overall operation of the computing device 20 and its associated components, including RAM 25, ROM 27, input/output device 29, communication interface 21, and/or memory 22. A data bus can interconnect processor(s) 23, RAM 25, ROM 27, memory 22, I/O device 29, and/or communication interface 21. In some embodiments, computing device 20 can represent, be incorporated in, and/or include various devices such as a desktop computer, a computer server, a mobile device, such as a laptop computer, a tablet computer, a smart phone, any other types of mobile computing devices, and the like, a mixing unit, and/or any other type of data processing device as appropriate Input/output (I/O) device 29 can include a microphone, keypad, touch screen, gas measurement sensor(s), and/or stylus through which a user of the computing device 20 can provide input, and can also include one or more of a speaker for providing audio output and a video display device for providing textual, audiovisual, and/or graphical output. Communication interface 21 can include one or more transceivers, digital signal processors, and/or additional circuitry and software for communicating via any network, wired or wireless, using any protocol as described herein. Software can be stored within memory 22 to provide instructions to processor 23 allowing computing device 20 to perform various actions. For example, memory 22 can store software used by the computing device 20, such as an operating system 24, application programs 26, and/or an associated internal database 28. The various hardware memory units in memory 22 can include volatile and nonvolatile, removable and non-removable media implemented in any method or technology for storage of information such as computer-readable instructions, data structures, program modules, or other data. Memory 22 can include one or more physical persistent memory devices and/or one or more non-persistent memory devices. Memory 22 can include, but is not limited to, random access memory (RAM) 25, read only memory (ROM) 27, electronically erasable programmable read only memory (EEPROM), flash memory or other memory technology, optical disk storage, magnetic cassettes, magnetic tape, magnetic disk storage or other magnetic storage devices, or any other medium that can be used to store the desired information and that can be accessed by processor 23.

Processor 23 can include a single central processing unit (CPU), which can be a single-core or multi-core processor, or can include multiple CPUs. Processor(s) 23 and associated components can allow the computing device 20 to execute a series of computer-readable instructions to perform some or all of the processes described herein. Although not shown in FIG. 2, various elements within memory 22 or other components in computing device 20, can include one or more caches, for example, CPU caches used by the processor 23, page caches used by the operating system 24, disk caches of a hard drive, and/or database caches used to cache content from database 28. For embodiments including a CPU cache, the CPU cache can be used by one or more processors 23 to reduce memory latency and access time. A processor 23 can retrieve data from or write data to the CPU cache rather than reading/writing to memory 22, which can improve the speed of these operations. In some examples, a database cache can be created in which certain data from a database 28 is cached in a separate smaller database in a memory separate from the database, such as in RAM 22 or on a separate computing device. For instance, in a multi-tiered application, a database cache on an application server can reduce data retrieval and data manipulation time by not needing to communicate over a network with a back-end database server. These types of caches and others can be included in various embodiments, and can provide potential advantages in certain implementations of devices, systems, and methods described herein, such as faster response times and less dependence on network conditions when transmitting and receiving data.

Although various components of computing device 20 are described separately, functionality of the various components can be combined and/or performed by a single component and/or multiple computing devices in communication without departing from the invention.

Breathing Gas Remixers

Figure 3:
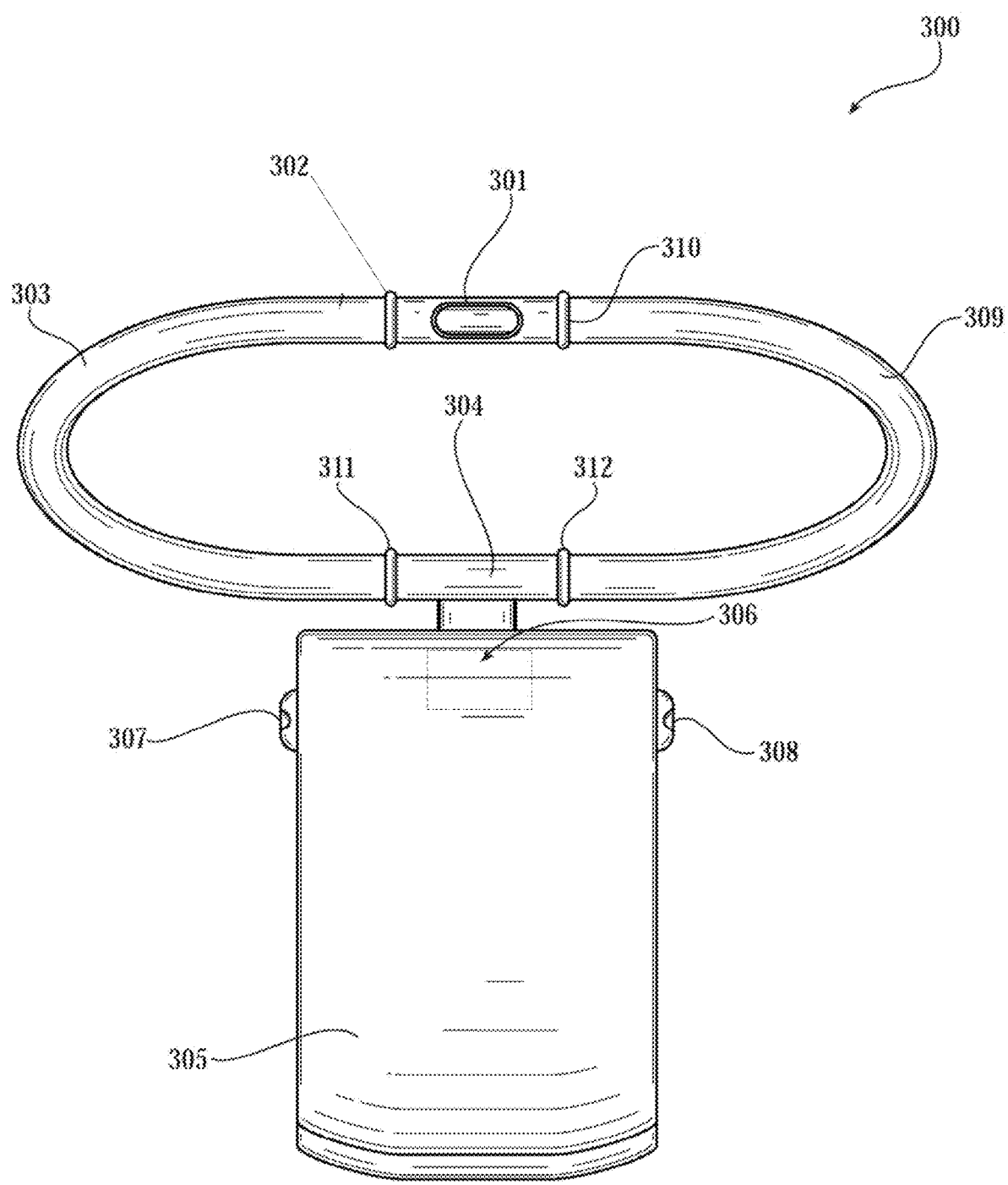
FIG. 3 is a line drawing of a breathing gas remixer in accordance with one or more aspects described herein.

FIG. 3 is a line drawing of a breathing gas remixer in accordance with one or more aspects described herein. The breathing gas remixer 300 includes a mouthpiece and/or mask 301. The mouthpiece and/or mask 301 can couple the breathing gas remixer to a user's mouth to allow the user to inhale and exhale through the breathing gas remixer 300. Exhalation gas transport tube 303 can be coupled to the mouthpiece 301 and gas reservoir interface connector 304 via one-way valve 302 and one-way valve 311 respectively, thereby allowing gas to flow from the mouthpiece 301 to the gas reservoir interface connector 304 through the exhalation gas transport tube 303. Gas reservoir interface connector 304 can be connected to gas reservoir 305 and/or mixing unit 306 (conceptually illustrated using dashed lines). The mixing unit 306 can be located internal and/or external to the gas reservoir 305. Gas reservoir 305 can include a gas release valve 307 and a fresh air intake port 308. Gas release value 307 can be pressure sensitive and be used to ensure that excess gas is not stored in gas reservoir 305. That is, the gas release valve 307 can allow gas to escape the gas reservoir 305 when the amount of gas stored in the gas reservoir 305 exceeds a threshold value. Inhalation gas transport tube 309 can be coupled to the mouthpiece 301 and gas reservoir interface connector via one-way valve 310 and one-way valve 312 respectively, thereby allowing gas to flow from the gas reservoir interface connector 304 to the mouthpiece 301 through the inhalation gas transport tube 309.

The gas reservoir can be flexible and/or rigid and can be constructed out of any materials, such as plastic, rubber, aluminum, steel, and the like. The gas transport tubes can be constructed out of any appropriate material, such as rubber, braided steel, and the like. However, it should be noted that any component can be constructed out of any combination of materials as appropriate.

The one-way valves 302, 310, 311, 312 can be fixed and include rotational couplers as appropriate. The usage of valves, with or without rotational couples, can allow movement of the exhalation gas transport tube 303 and/or inhalation gas transport tube 309 as the gas reservoir 305 is positioned in various locations in space. In a number of embodiments, inhalation gas transport tube 309 and exhalation gas transport tube 303 are encased within a single larger tube to give the appearance of one hose coupling the mouthpiece 301 and the gas reservoir interface connector 304. In many embodiments, one-way valve 302 and/or one-way valve 310 are located within mouthpiece 301. In several embodiments, one-way valve 311 and/or one-way valve 312 are located within gas reservoir interface connector 304. In many embodiments, gas reservoir interface connector 304 is located within mixing unit 306 and/or gas reservoir 305. In many embodiments, one or more filters (not pictured) can be added to reduce humidity and/or reduce particulates in the gas mix.

Figure 4:
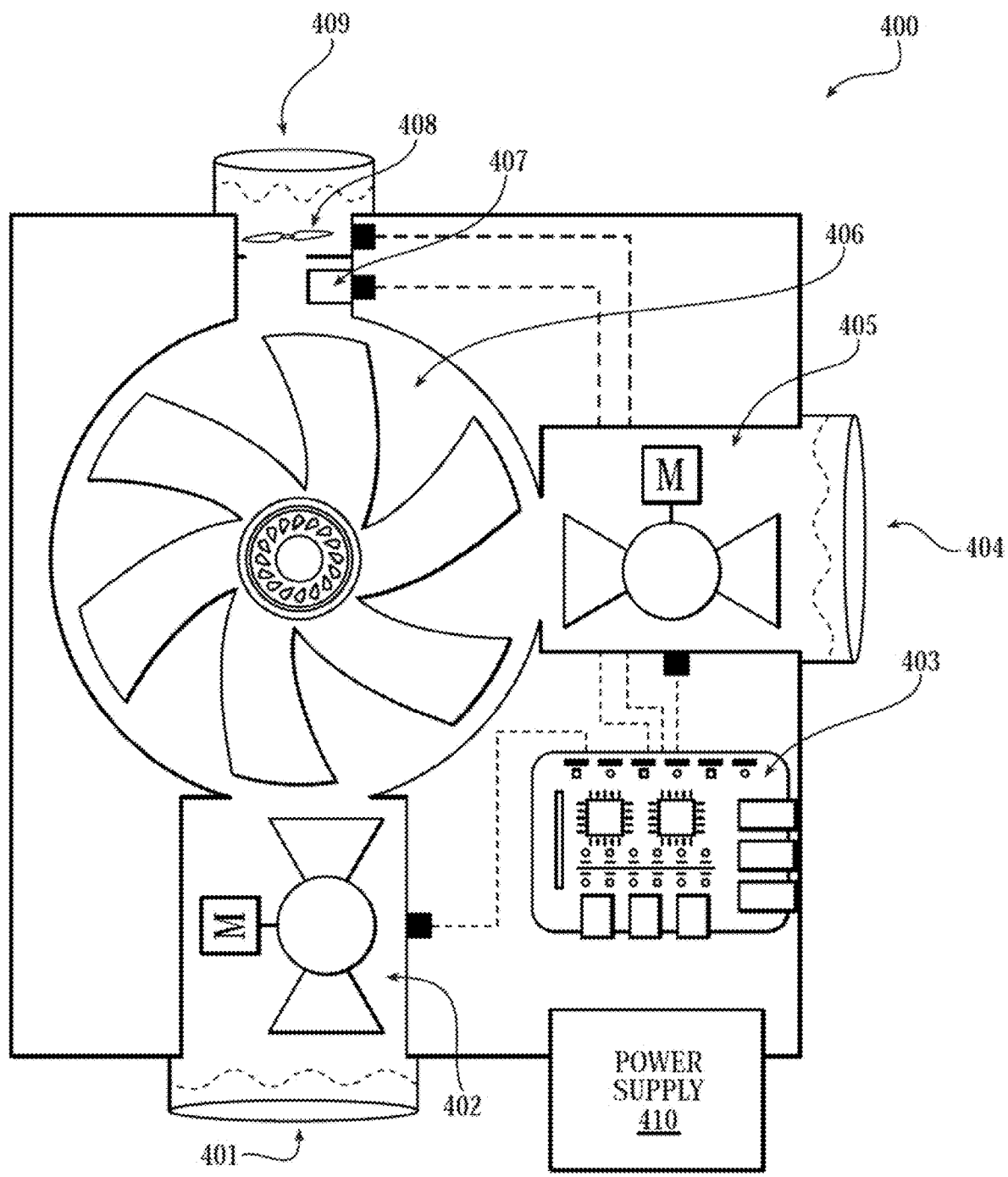
FIG. 4 is a schematic of a mixing unit in accordance with one or more aspects described herein.

FIG. 4 is a schematic of a mixing unit in accordance with one or more aspects described herein. In FIG. 4, dotted lines represent internal portions of the device and dashed lines with square boxes represent electrical connections. The mixing unit 400 includes a reservoir air intake port 401. Coupled to the reservoir air intake port 401 is a gas intake valve 402. In several embodiments, the gas intake valve 402 is motorized. Mixing unit 400 further include a controller 403. Controller 403 can take any of a variety of forms, including a microcontroller and/or a processor. In many embodiments, controller 403 can include any components of a computing device as described herein. Controller 403 can control the mixing of gases using one or more models as described herein. In a variety of embodiments, the controller 403 is located external to the mixing unit 400. Mixing unit 400 can further include fresh air intake 404 and fresh air intake valve 405. In a variety of embodiments, the fresh air intake valve 405 is motorized. Mixing unit 400 further includes a mixing container and rotor 406 for mixing gases. The rotor can be powered via the power supply 410 and/or via the flow of gas through the system. Mixture sensor 407 can be used to determine the concentration of gases in the gas mixture produced by mixing container and rotor 406. In several embodiments, mixture sensor 407 determines the level of a target gas, such as $CO_2$, within the gas mixture. Airflow sensor 408 can determine the volume of gas flowing from mixing container and rotor 406 and through inhalation gas port 409. Mixing unit 400 can also include power supply 410 that supplies power to any of the components of mixing unit 400. Power supply 410 can provide AC and/or DC power as appropriate. Power can be provided by a transformer plugged into an electrical outlet, battery powered using a battery and charging circuitry, and/or any other power supply as appropriate. In many embodiments, power supply 410 includes one or more energy harvesters to harvest energy from the exhalation and inspiration of gas within the system, from motion of the user and/or breathing gas remixer, and/or from the surrounding environment.

The mixing container and rotor 406 can take in fresh air via fresh air port 404 and exhaled air via reservoir air intake port 401. The fresh air and exhaled air can be mixed to generate a gas mix having a desired composition as measured by mixing sensor 407. Mixing sensor 407 and/or airflow sensor 408 can be coupled to controller 403 to provide data to the controller 403. The controller 403 can determine target gas mixes, and, once the target gas mix has been created, can cause the delivery of the gas mix in a determined volume via inhalation gas port 409. In the event that the mixture has too high a concentration of a particular gas, a secondary mixture sensor (not shown) can be used downstream of the mixing container and rotor 406 as a safety feature and coupled with a valve to allow direct inhalation of fresh air.

Figure 5A:
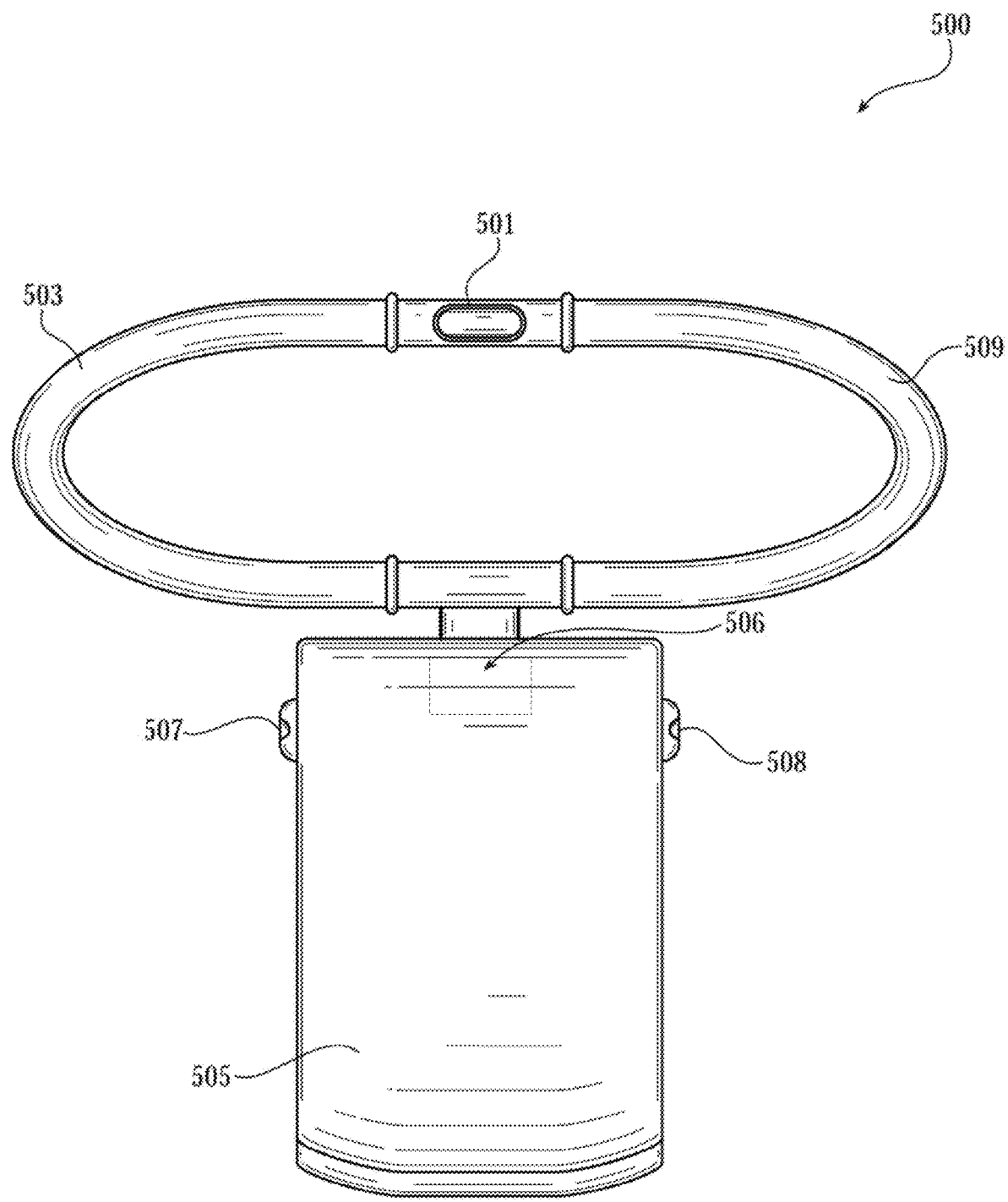
FIG. 5A-C are illustrations of the usage of a breathing gas remixer in accordance with one or more aspects described herein.
Figure 5B:
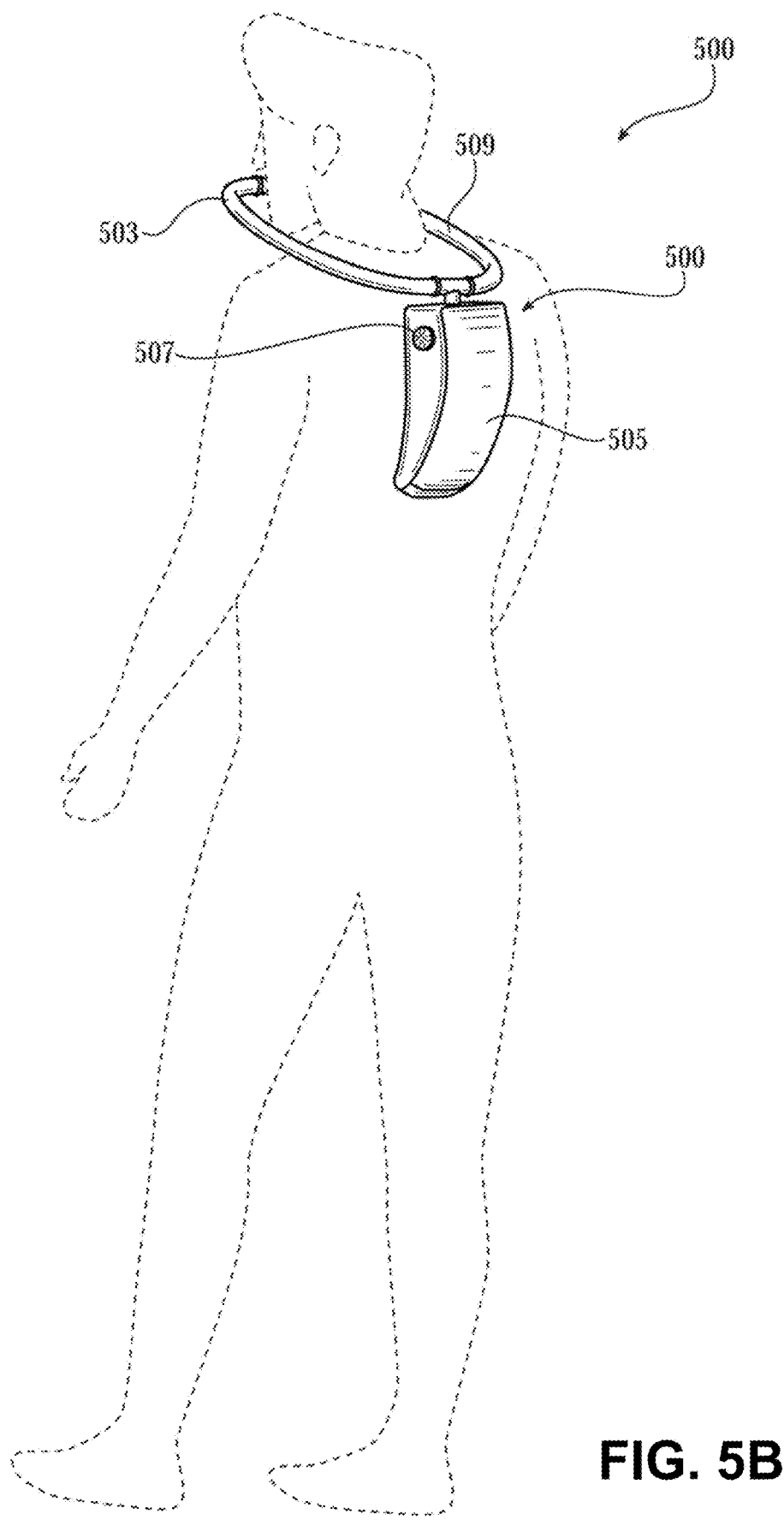
Figure 5C:
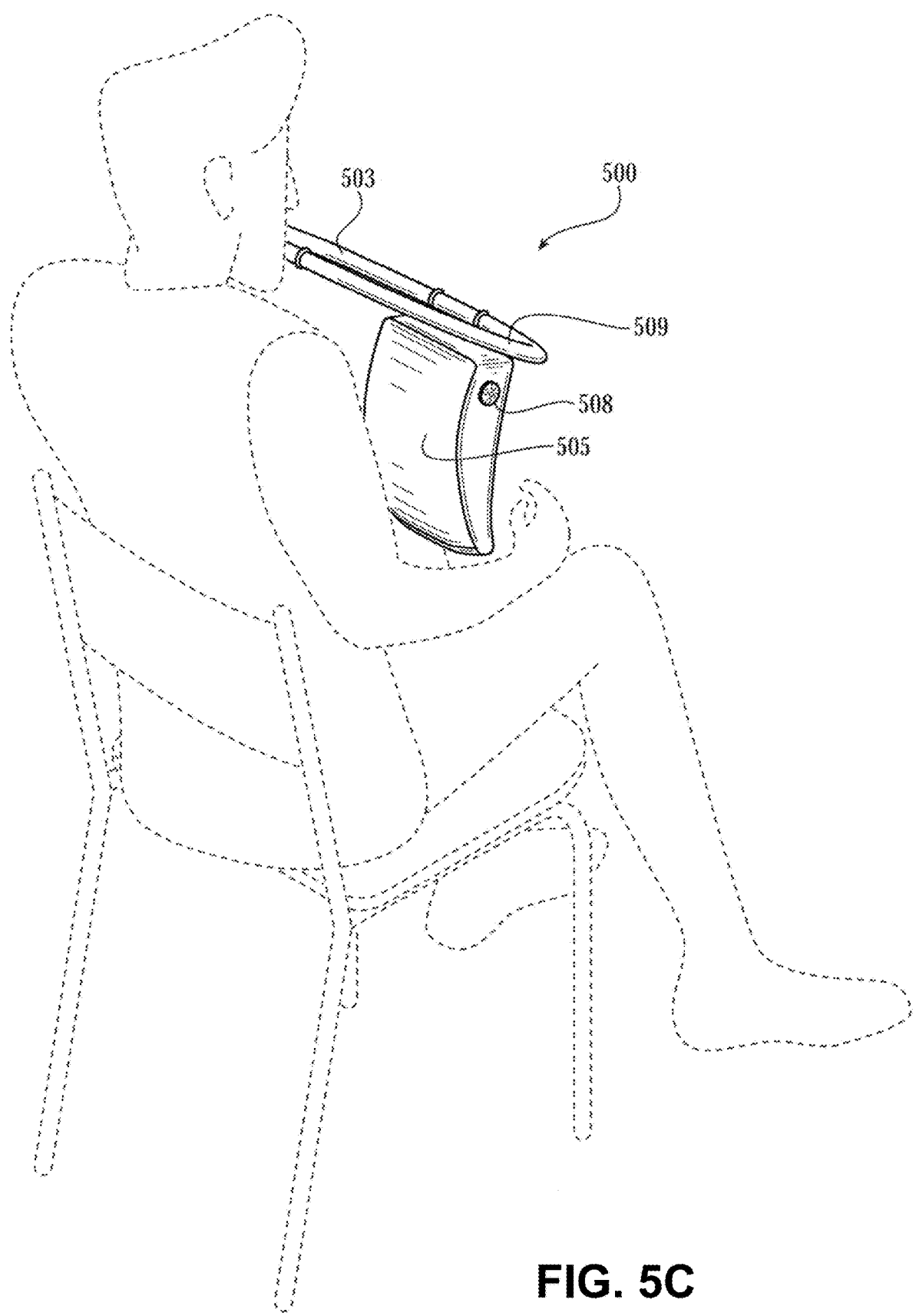

FIGS. 5A-C are illustrations of the usage of a breathing gas remixer in accordance with one or more aspects described herein. As shown in FIG. 5A, illustration 500 includes a breathing gas remixer. The construction of the breathing gas remixer in illustration 500 is described herein, particularly with respect to FIGS. 3 and 4. When the person exhales, the exhaled air is captured in mouthpiece or mask 501 and propelled through the exhalation gas transport tube 503 into the gas reservoir 505 where the gas is held. When the gas reservoir 505 is filled, typically beyond 6 liters of gas, excess gas can be released through gas release valve 507. When the person inhales, gas stored within the gas reservoir 505 is pulled into mixing unit 506 (conceptually illustrated using dashed lines). Fresh air can be pulled into the mixing unit 506 through the fresh air intake 508. In several embodiments, bottles of gas, such as bottled carbon dioxide and/or air/oxygen sources, can be coupled to the fresh air intake 508. Both sources lead to a mixing container with a rotor for mixing the gases from the two sources. The amount of gas taken from each source can be determined using a controller with a mixture sensor and/or airflow sensor to determine the amount by which to open each of the valves to achieve the desired concentration of gas components (such as CO2) within the gas mix within the mixing container 506. In a variety of embodiments, the controller uses one or more models to determine the proportion of various breathing gases within the gas mix. The gas mix can be inhaled from the mixing unit 506 through the inhalation gas tube 509 into mouthpiece or mask 501 for the user to breathe in.

The breathing gas remixer can be worn in a variety of orientations, such as on the user's back while the user is standing, as shown in FIG. 5B, and/or in the user's lap, such as when the user is sitting as shown in FIG. 5C. As shown in FIG. 5B, while the gas reservoir 505 is located on the user's back, the mouthpiece can be located in the user's mouth and connected by one or more over the shoulder hoses to the gas reservoir providing the inhaled air. This orientation can be particularly useful during exercise or while working. As shown in FIG. 5C, while the gas reservoir 505 is located on the user's lap, the mouthpiece can be located in the user's mouth and connected by one or more hoses to the gas reservoir 505 providing the inhaled air. This orientation can be particularly useful for those patients in recovery and/or experiencing health problems. The breathing gas remixer can also be located remote from the user and/or mounted in a fixed location, such as a pole, wall, or otherwise held in place or transported as appropriate.

Although a variety of usages and orientations of breathing gas remixers are described with respect to FIGS. 5A-C, it should be noted that a variety of other orientations and integrations with other breathing systems can be utilized in accordance with a variety of embodiments of the invention. For example, breathing gas remixers can work in combination with continuous positive airway pressure (CPAP) machines (home or clinically based, portable or not), sleep monitoring systems, sleep apnea treatments, ventilators, and similar types of ventilators and/or home oxygen therapies to integrate ramp, bursts or windows of continuous fixed $CO_2$ levels with inspiration with continuous feedback to intermittently enhance cerebral blood flow with the intent of preserving cerebral blood flow during therapies associated with declines in cerebral blood flow and challenges related to cognitive decline over time. Similarly, breathing gas remixers can be used during general anesthesia, such as in conjunction with anesthesia machines, to provide similar benefits.

Operating Breathing Gas Remixers

Breathing gas remixers can provide a specific gas mix for users to inhale. In particular, breathing gas remixers can modify gas exhaled by the user to have specific concentrations of particular gases, such as $CO_2$. In a variety of embodiments, the breathing gas remixer can mix the exhaled gas to a particular combination of gases as specified in a breathing model. The breathing model can be determined based on the respiration of the user, medical conditions being experienced by the user, and/or in accordance with specific treatment goals as described herein.

Breathing, even under resting conditions, is complex and while primarily under autonomic control, the breathing gas remixers are designed to optimize gas exchange ($O_2$ and/or $CO_2$) with minimal cost. Breathing patterns (e.g. changes in respiratory rate and tidal volume) and/or operational lung volume (where one breathes on the pressure volume relationships of the lung or within the constraints of total lung capacity and residual volume) play a major role in adequacy of gas exchange. There can also be dynamic changes in matching the ventilation in the lungs to perfusion in vessels and dead space that need to be overcome from the mouth, nose, upper airways and conducting airways. Volitional changes on a per breath basis further impact the dynamic regulation of breathing. These breathing dynamics complicate the needed respiratory control can be addressed using the breathing model.

Breathing gas remixers can take advantage of a complex regulation of rebreathing to alter inspired $CO_2$ levels while allowing an influx of room air to maintain $O_2$ near normal. Breathing gas remixers can also provide an independent control of inspired $O_2$. As the $CO_2$ levels in a user begin to rise from the gas mix inhaled through the breathing gas remixer, ventilation can be stimulated through central chemoreceptors which attempt to minimize the rise in $CO_2$ in the arterial blood. However, the increase in $CO_2$ can be precisely regulated by the breathing gas remixer at a fixed rate of rise and within a defined range with an individual exposed to intervals with ramping levels of $CO_2$ concentration such that, while $CO_2$ rises, $O_2$ levels remain relatively constant. The range within the ramp can be slowly extended, and/or the number of intervals increased, over a treatment period. The treatment period can be any period of time but is typically between one and six weeks. The gas mix provided by the breathing gas remixer not only stimulates the central chemoreceptors, but also the neural pathways involved in synchronized breathing, such as breathing involving the upper airways, accessory inspiratory muscle, and/or diaphragm. At the same time, cerebral circulation can be markedly increased. Additionally, breathing gas remixers can also introduce complex changes in the respiratory quotient influencing $VO_2$ and $VCO_2$, including changes in tidal volume and operational volume.

Figure 6:
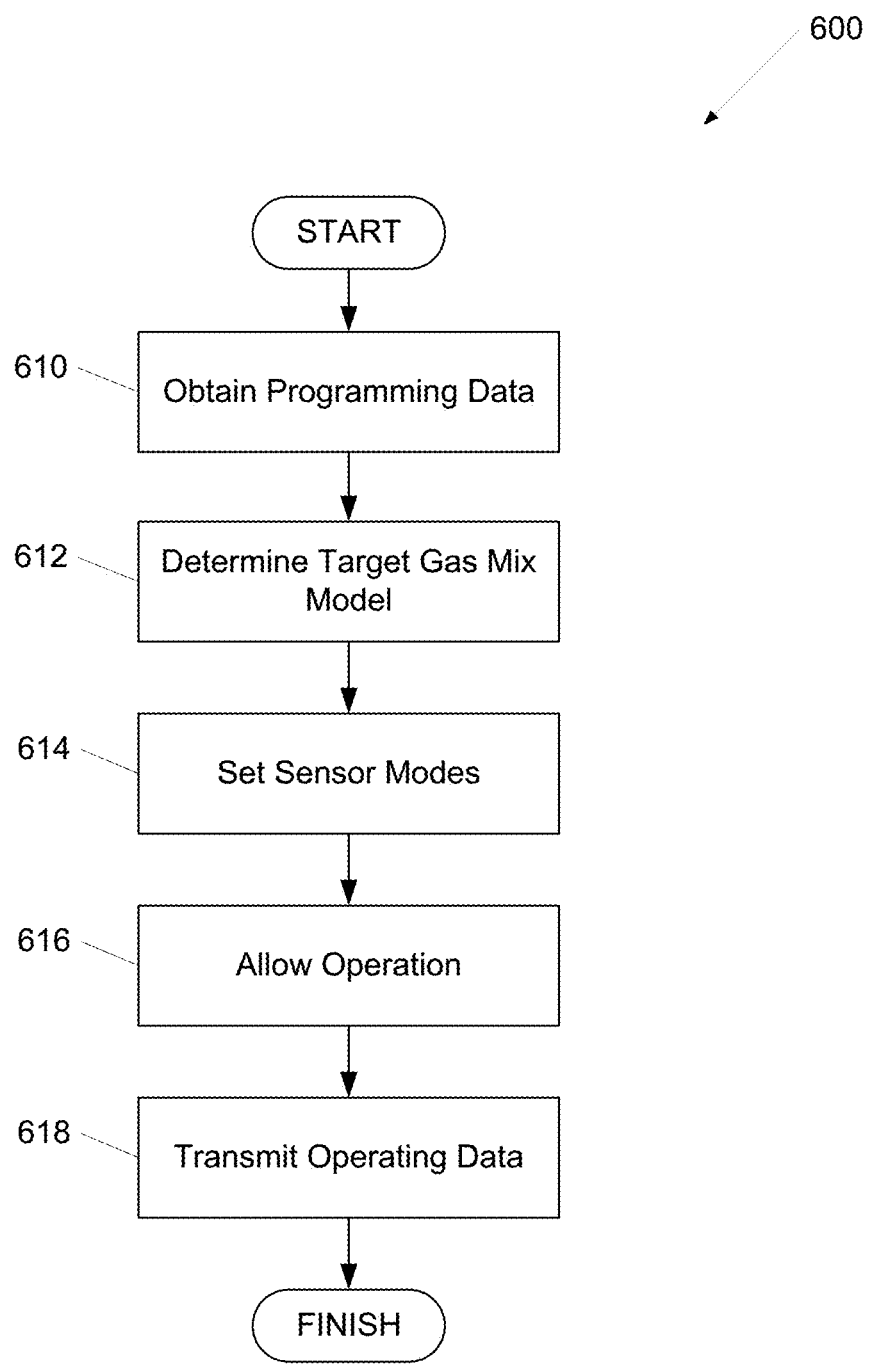
FIG. 6 depicts a flow chart for programming a breathing gas remixer according to one or more aspects described herein.

FIG. 6 depicts a flow chart for programming a breathing gas remixer according to one or more aspects described herein. Some or all of the steps of process 600 can be performed using any of the computing devices and/or combination thereof described herein. In a variety of embodiments, some or all of the steps described below can be combined and/or divided into sub-steps as appropriate.

Programming data can be obtained (610). The programming data can include a variety of instructions for programming a controller of a mixing unit. The programming data can be obtained from any of a variety of sources, such as a mobile device and/or a processing server system. The instructions can indicate any operating parameters of the breathing gas remixer as described herein. In many embodiments, the programming data includes information that allows external devices, such as a mobile device, to obtain data generated during the operation of the operating gas remixer. The programming data can include a model indicating target gas mixes based on the patient's medical condition and/or breathing characteristics as described herein. Any of a variety of breathing models can be used in accordance with embodiments of the invention, such as those described in "Evaluation of Cardiac Output from a Tidally Ventilated Homogeneous Lung Model" by Benallal et al., the disclosure of which is hereby incorporated by reference in its entirety.

A target gas mix model can be determined (612). The target gas mix can be indicated in the programming data, the model, and/or calculated based on the instructions in the programming data. The target gas mix can indicate the desired concentrations of one or more gases within a gas mix. The target gas mix can also include temperature, humidity, and/or pressure settings for the gas mix. The model utilized by the breathing gas remixer can include an amount of inspired air to be provided by the breathing gas remixer. Additionally, the model can indicate an estimated concentration of the expired gas concentration and the amount (if any) of additional gases (e.g. 02, $CO_2$, etc.) to generate the desired inspired gas mixture based on the expired gas.

Sensor modes can be set (614). Sensor modes can include programming sensors to detect particular gases and/or allow particular volumes of gas to flow as appropriate. In a variety of embodiments, the sensor modes are set based on particular parameters for each of the sensors as defined in the model.

Operation of the breathing gas remixer can be allowed (616). Operation of the breathing gas remixer can be disabled until the controller is programmed. For example, gas mixes can be user-dependent and the safety of the breathing gas remixer can be improved by ensuring that the breathing gas remixer is programmed for a particular user prior to allowing operation of the breathing gas remixer.

Operating data can be transmitted (618). Data generated during the operation on the breathing gas remixer state, including the detected gas levels and/or the inhalation airflow rate/volume can be determined. This data can be transmitted to a variety of computing devices, such as a mobile device and/or processing server system. These computing devices can display the data and/or generate additional programming data. In several embodiments, the operating data can be used in a feedback loop in which the operating state as well as temporal changes (e.g. desired rate of blood flow change, breath rate, etc.) can be used to dynamically adjust the desired concentration of gases. The feedback loop can operate on data internal to the breathing gas remixer and/or using data obtained from the external computing devices.

Administering Treatments Using Breathing Gas Remixers

As described herein, breathing gas remixers can be used to increase blood flow in patients. In addition to being able to increase blood flow, there can be a variety of secondary benefits in post-ventilator patient recovery as a failure to wean from ventilators is partly a neural issue (e.g. motor unit recruitment, synchrony etc.), rather than an end organ (muscle) issue. Increasing $CO_2$ levels in breathing gas mixes can cause peripheral vasodilation, which can be used as an afterload reduction to help patients with heart failure and/or other breathing difficulties. A variety of other disease states or injuries, such as obesity and obstructive sleep apnea, can be treated by administering treatments using breathing gas remixers as described herein, such as in concussion recovery or after stroke. Therapeutic benefits may be achieved through fixed exposures of inspired gas or through various progressive protocols including "ramp" exposures (e.g. gradual progressive increases in inspired $CO_2$) and/or through progressive intervals of exposure (e.g. on/off transients). Additional benefits, such as fixing the inspired $CO_2$ and lowering the inspired oxygen through various protocols may stimulate a host of adaptive physiological responses such as EPO levels, regenerative capacity of tissues, red cells, and/or red cell turn over.

For example, severe COVID-19 infections are associated with ventilator dependence and significant neurocognitive and respiratory impairment post-recovery with reports of ongoing reductions in mental performance, loss of lung function, respiratory muscle dyscoordination, and/or shortness of breath. These problems have been called "Post-Intensive Care Syndrome" or PICS. The prevalence of cognitive dysfunction in PICS is extreme: 70%-100% at discharge; 46% to 80% one year out; and 20% at five years after discharge. This cognitive dysfunction spans a variety of domains including memory, attention, verbal fluency, calculation, and executive function. Many have trouble returning to their pre-hospitalization jobs, cannot perform tasks like simple arithmetic, and can't cannot remember both short (e.g. why they are at the store) and long-term memories (e.g. aspects from their college training). Universally, these patients wish for a return to their pre-hospitalization level of cognition. While the cause of the cognitive deficits seen in PICS is still unclear, to address both the cognitive and respiratory complications in these patients, innovative treatments can be administered using breathing gas remixers based on two primary factors. First, dementias, stroke, and concussion are also associated with cognitive impairment, and, often, dyssynchronous respiratory control and function (upper airway muscles, laryngeal, diaphragm). Second, vascular dysfunctions resulting in reduced and/or heterogeneous blood flow to the brain can be associated with cognitive impairment. These two insights have led to studies demonstrating that improving cerebral blood flow and cerebral vascular function improves cognitive performance through a number of mechanistic pathways (e.g., eliminating damaged and senescent cells, improved endothelial function, enhanced oxygenation, and the like).

Figure 7:
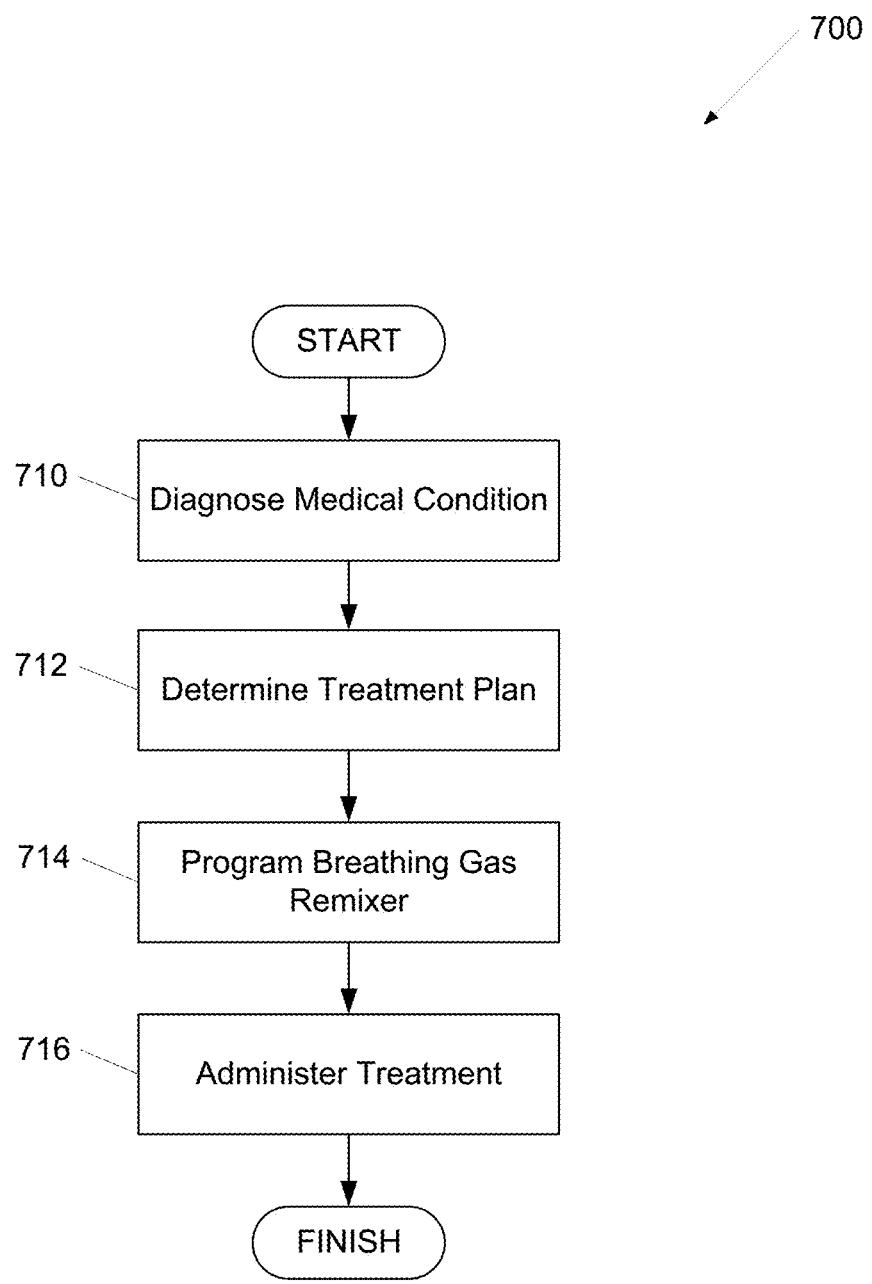
FIG. 7 depicts a flow chart for diagnosing and treating medical conditions according to one or more aspects described herein.

FIG. 7 depicts a flow chart for diagnosing and treating medical conditions according to one or more aspects of the disclosure. Some or all of the steps of process 700 can be performed using any of the computing devices and/or combination thereof described herein. In a variety of embodiments, some or all of the steps described below can be combined and/or divided into sub-steps as appropriate.

A medical condition can be diagnosed (710). Medical condition can include vascular dementia. Vascular dementia includes a number of conditions associated with diminished reasoning, planning, judgment, memory, and other thought processes. Vascular dementia often includes brain damage caused by impaired or reduced blood flow to the brain. Reduced blood flow can be caused by a variety of conditions, such as stroke, which can block blood vessels in the brain, and/or narrowed or chronically damaged brain blood vessels. Conditions that narrow or inflict long-term damage on blood vessels can also include aging, high blood pressure, atherosclerosis, diabetes, brain hemorrhage, and the like.

A treatment plan can be determined (712). The treatment plan can be determined based on the diagnosed medical conditions. The treatment plan can include a target blood flow. The target blood flow can be determined to improve overall blood flow, to clear blockages in the vascular system, and the like. The treatment plan can include particular gas levels to be inhaled for a particular period of time. For example, normal regional cerebral blood flow (CBF) is typically in the range of 50-60 cc/100 g/min. During moderate exercise, CBF can increase by 10-30%. A treatment plan can include measuring a patient's CBF and calculating a treatment plan to administer a $CO_2$-enriched gas mix to increase the patient's CBF by an amount relative to the patient's baseline CBF, such as an improvement of 10-300% over baseline CBF. In several embodiments, the treatment plan includes determining a set of graded CBF target levels and administering multiple treatments of $CO_2$-enriched gas mixes to increase the patient's CBF over multiple treatment sessions. For example, four treatment sessions can be prescribed to increase the patient's CBF by 40%, the four treatments increasing the patient's CBF by 10-15%, 15-20%, 20-30%, and 30-40% respectively. In a variety of embodiments, the treatment plan is determined based on therapeutically-effective treatments administered to a cohort of patients similar to the patient and having the same diagnosed medical condition. Each patient in the cohort of patients may have been diagnosed with the same medical condition and/or similar medical conditions. Additional characteristics of the patients, such as age, gender, race, weight, underlying medical conditions, geographic location, and the like can also be used to define the patients included in a particular cohort as appropriate.

A breathing gas remixer can be programmed (714). The breathing gas remixer can be programmed using programming data indicating the therapeutically effective blood flow, gas mix, and/or any other criteria in the treatment plan. For example, the breathing gas remixer can be programed to provide certain level of $CO_2$ and/or maintain a particular exhaled gas mix. In several embodiments, the breathing gas is programmed to calculate the patient's CBF based on the relative gas levels of their exhaled breath. In a variety of embodiments, the treatment plan can be determined based on a model determined based on the diagnosed medical condition. In a variety of embodiments, the model is generated based on models for a cohort of patients similar to the patient and having the same diagnosed medical condition. The model can be modified and/or customized to a particular patient based on their specific condition and/or breathing capability as described herein. The breathing gas remixer can be programmed as described herein.

Treatments can be administered (716). The gas mix can be administered to the patient in a therapeutically effective dose determined based on the treatment plan. The therapeutically effective dose can be determined based on the processed breath data for the person such that the recommended and/or administered treatment is personalized to the person. In a variety of embodiments, the breathing gas remixer dynamically adjusts the amount of $CO_2$ in the gas mix to maintain the patient's calculated CBF within a particular range indicated in the treatment plan. The treatments can be administered during the operation of the breathing gas remixer as described herein.

One or more aspects discussed herein can be embodied in computer-usable or readable data and/or computer-executable instructions, such as in one or more program modules, executed by one or more computers or other devices as described herein. Generally, program modules include routines, programs, objects, components, data structures, and the like that perform particular tasks or implement particular abstract data types when executed by a processor in a computer or other device. The modules can be written in a source code programming language that is subsequently compiled for execution, or can be written in a scripting language such as (but not limited to) HTML or XML. The computer executable instructions can be stored on a computer readable medium such as a hard disk, optical disk, removable storage media, solid-state memory, RAM, and the like. As will be appreciated by one of skill in the art, the functionality of the program modules can be combined or distributed as desired in various embodiments. In addition, the functionality can be embodied in whole or in part in firmware or hardware equivalents such as integrated circuits, field programmable gate arrays (FPGA), and the like. Particular data structures can be used to more effectively implement one or more aspects discussed herein, and such data structures are contemplated within the scope of computer executable instructions and computer-usable data described herein. Various aspects discussed herein can be embodied as a method, a computing device, a system, and/or a computer program product.

Although the present invention has been described in certain specific aspects, many additional modifications and variations would be apparent to those skilled in the art. In particular, any of the various processes described above can be performed in alternative sequences and/or in parallel (on different computing devices) in order to achieve similar results in a manner that is more appropriate to the requirements of a specific application. It is therefore to be understood that the present invention can be practiced otherwise than specifically described without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A breathing gas remixer, comprising:
    a gas reservoir comprising a gas release valve and a fresh intake port;
    a gas-reservoir tee interface comprising a stem branch coupled to a top of the gas reservoir, a first leg and a second leg opposite the first leg;
    a mouthpiece having a longitudinal axis, a first port on one end, a second port opposite the first port and a mouthpiece opening that is normal to the longitudinal axis;
    a mixing unit disposed internal to the gas reservoir and comprising an impeller, a microcontroller, a sensor, and a power supply supplying power to the impeller and the microcontroller;
    an exhalation gas transport tube connected at a first exhalation-tube end to the first leg by a first connector and coupled at an opposite exhalation-tube end to the first port by a second connector, the exhalation gas transport tube fluidly coupling the mouthpiece opening and the gas reservoir via first and second one-way exhalation valves;
    an inhalation gas transport tube coupled at a first inhalation-tube end to the second leg by a third connector and coupled at an opposite inhalation-tube end to the second port by a fourth connector, the inhalation gas transport tube fluidly coupling the mouthpiece opening and the mixing unit via first and second one-way inhalation valves;
    wherein the gas reservoir is configured to store exhaled gas from a user that is received via the mouthpiece;
    wherein the mixing unit is configured to generate a gas mix by mixing the exhaled gas with fresh air obtained through the fresh air intake port, using the impeller;
    wherein the mixing unit delivers the gas mix to the mouthpiece via the inhalation gas transport tube; and wherein each of the first connector, the second connector, the third connector and the fourth connector is a rotational connector, such that in a first configuration, the gas reservoir can be disposed on the user's back with the exhalation gas tube and the inhalation gas tube being disposed in an over-the-shoulder manner; or in a second configuration, the gas reservoir can be disposed in the user's lap with the exhalation gas tube, the inhalation gas tube and the mouthpiece rotated about 180 degrees relative to the first configuration.

2. The breathing gas remixer of claim 1, wherein the mouthpiece comprises a mask.

3. The breathing gas remixer of claim 1, wherein the gas reservoir is flexible and is constructed using at least one material selected from the group consisting of plastic and rubber.

4. The breathing gas remixer of claim 1, wherein the gas reservoir is rigid and is constructed using at least one material selected from the group consisting of plastic, aluminum, and steel.

5. The breathing gas remixer of claim 1, wherein the exhalation gas transport tube is constructed using at least one material selected from the group consisting of rubber and braided steel.

6. The breathing gas remixer of claim 1, wherein the inhalation gas transport tube is constructed using at least one material selected from the group consisting of rubber and braided steel.

7. The breathing gas remixer of claim 1, wherein the gas release valve releases gas from the gas reservoir when an amount of gas stored using the gas reservoir exceeds a threshold value.

8. The breathing gas remixer of claim 7, wherein the amount of gas is approximately six liters.

9. The breathing gas remixer of claim 1, wherein the power supply generates power based on the flow of exhalation gas.

10. The breathing gas remixer of claim 1, wherein the power supply generates power based on the flow of the gas mix.

* * * * *